United States Patent [19]

Boehm et al.

[11] 4,222,967
[45] Sep. 16, 1980

[54] PROCESS FOR PREPARING BROMINE- AND FLUORINE-CONTAINING HALOGENATED HYDROCARBONS

[75] Inventors: Horst Boehm; Karl-Heinz Hellberg, both of Hanover, Fed. Rep. of Germany

[73] Assignee: Kali-Chemie AG, Hanover, Fed. Rep. of Germany

[21] Appl. No.: 810,565

[22] Filed: Jun. 27, 1977

[30] Foreign Application Priority Data

Jul. 2, 1976 [DE] Fed. Rep. of Germany ....... 2629774

[51] Int. Cl.² .............................................. C07C 17/10
[52] U.S. Cl. ................................................. 260/653.8
[58] Field of Search ................. 260/653, 653.8, 658 R

[56] References Cited

U.S. PATENT DOCUMENTS

| | | | |
|---|---|---|---|
| 2,553,518 | 5/1951 | Lake et al. | 260/658 R |
| 2,729,687 | 1/1956 | Sterling | 260/653.8 |
| 2,875,254 | 2/1959 | Gradishar | 260/653.8 |
| 2,921,098 | 1/1960 | Suckling et al. | 260/653.8 |
| 3,000,980 | 9/1961 | Asadorian et al. | 260/658 R |
| 3,370,096 | 2/1968 | Donaldson et al. | 260/658 R |
| 3,755,474 | 8/1973 | Bjornson | 260/658 R |

*Primary Examiner*—Delbert E. Gantz
*Assistant Examiner*—Joseph A. Boska
*Attorney, Agent, or Firm*—Schwartz, Jeffery, Schwaab, Mack, Blumenthal & Koch

[57] ABSTRACT

A process for brominating fluorine- and chlorine-containing halogenated hydrocarbons of formula (I)

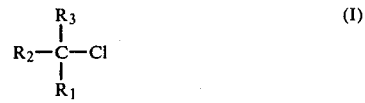

wherein $R_1$ represents hydrogen, fluorine, chlorine, bromine, lower alkyl, or at least partially fluorinated lower alkyl; $R_2$ represents hydrogen, fluorine, chlorine, or bromine; and, $R_3$ represents fluorine or perfluorinated lower alkyl, to form the corresponding compounds of formula (II)

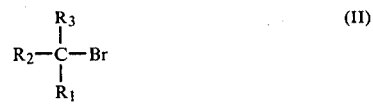

wherein $R_1$, $R_2$ and $R_3$ are as defined above is disclosed. According to this process, compounds of formula (I) are reacted in gaseous form at relatively mild reaction conditions, e.g., reaction temperatures of between 100°–500° C. with hydrogen bromide in the presence of a catalyst comprising at least one component selected from the group consisting of
(a) active carbon,
(b) silica gel,
(c) active alumina, and
(d) a bromide of an element selected from the group consisting of Li, Na, K, Rb, Cs, Mg, Ca, Sr, Ba, Zn, Cd, Cu, Ag, Al, Tl(I), Pb, Cr, Mn, Fe, Co, Ni, rare earth metals and metals of the platinum group.

7 Claims, No Drawings

PROCESS FOR PREPARING BROMINE-AND FLUORINE-CONTAINING HALOGENATED HYDROCARBONS

BACKGROUND OF THE INVENTION

The present invention relates to a process for brominating fluorine- and chlorine-containing halogenated hydrocarbons by exchanging a chlorine therein with bromine by reaction with hydrogen bromide in the presence of a catalyst.

Catalysts for catalyzing the exchange of chlorine with bromine in chlorinated hydrocarbons which do not contain any fluorine are known in the art (see, e.g., Houben-Weyl, Methoden der Organischen Chemie, 4th Ed., vol. V/4, p. 356, or Z. E. Jolles in "Bromine and Its Compounds," publisher Ernest Benn Ltd., London, 1966, p. 384).

Yet, for reacting fluorine- and chlorine-containing hydrocarbons wherein the reactivity of the chlorine is particularly low, only the process which is disclosed in U.S. Pat. No. 2,729,687 is known up until now. According to this process, the substitution of chlorine by bromine is effected at a temperature of between 500° and about 650° C.

Disadvantages of this process are the high reaction temperature and, connected therewith, the very limited choice of reactor materials, as well as low degree of substitution and a low selectivity with regard to substituting only one of several chlorine atoms within a halogenated fluorohydrocarbon containing more than one chlorine atom per molecule. For example, when dichloro-difluoromethane is reacted with hydrogen bromide at a molar ration $HBr:CCl_2F_2$ of 0.8 at a temperature of 600° C. and a contact period of 22 seconds, only 5 mole percent are converted into bromo-chloro-difluoromethane and another 5 mole percent into dibromo-difluoromethane.

SUMMARY OF THE INVENTION

It is an object of the present invention to provide a process for replacing with bromine a chlorine atom in a fluorine- and chlorine-containing halogenated hydrocarbon by reaction with hydrogen bromide which avoids these drawbacks of the prior art processes.

It is a further object of the present invention to provide such a process which can be effected at a relatively low temperature.

It is a further object of the present invention to provide such a process which yields a high amount of brominated reaction products.

It is still a further object of the present invention to provide such a process which is highly selective with regard to substituting only one of several chlorine atoms which are present in a halogenated fluorine-containing hydrocarbon.

It is yet a further object of the present invention to provide such a process which can be continuously operated for a relatively long period of time and which does not require expensive reactor materials.

In order to accomplish the foregoing objects according to the present invention, there is provided a process for brominating fluorine-and chlorine-containing halogenated hydrocarbons which comprises the step of contacting at least one halogenated fluorohydrocarbon compound of formula (I)

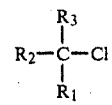

wherein $R_1$ represents hydrogen, fluorine, chlorine, bromine, lower alkyl, or at least partially fluorinated lower alkyl; $R_2$ represents hydrogen, fluorine, chlorine, or bromine; and, $R_3$ represents fluorine or perfluorinated lower alkyl, in gaseous form and hydrogen bromide with a catalyst comprising at least one component selected from the group consisting of (a) active carbon,
(b) silica gel,
(c) active alumina,
(d) a bromide of a metal selected from the group consisting of Li, Na, K, Rb, Cs, Mg, Ca, Sr, Ba, Zn, Cd, Cu, Ag, Al, Tl(I), Pb, Cr, Mn, Fe, Co, Ni, rare earth metals and metals of the platinum groups, and
(e) mixtures thereof, at a contact time and a reaction temperature sufficient for transforming the reactants into sufficiently stable gaseous compounds and for substituting the chlorine in a compound of formula (I) by bromine to form a compound of formula (II)

wherein $R_1$, $R_2$ and $R_3$ are as defined above.

Instead of an above-defined bromide, a compound of a metal selected from the group as defined above under (d) which is at least partially convertible, in situ, into the corresponding bromide by reaction with bromine or hydrogen bromide can be used as a catalyst component.

The reaction temperature may range from about 100° to about 500° C. The contact time may range from about 1 to about 100 seconds.

The process may be carried out in a continuous operation, whereby unreacted starting materials and/or optionally over brominated reaction products can be recycled into the reaction. Thus, high yields of the desired compounds of formula (II) wherein only one chlorine atom of the starting material is substituted by bromine are achieved.

Further objects, features and advantages of the present invention will become apparent from the following detailed description of the invention and its preferred embodiments.

DETAILED DESCRIPTION OF PREFERRED EMBODIMENTS

Within the process according to the present invention, all such compounds of formula (I) can be brominated which themselves, as well as their respective reaction products of formula (II) under the given reaction conditions, are transformable into the gaseous phase and are sufficiently stable. Preferably, these compounds contain 1–3 carbon atoms per molecule.

Such bromo- and bromo-chloro-fluorohydrocarbons which can be prepared according to the process of the present invention are valuable fire extinguishing or cooling agents, e.g., brominated fluoromethane compounds, such as, bromo-chloro-difluoromethane ($CBrClF_2$) or bromo-trifluoromethane ($CBrF_3$), or inhalation-narcotics like, e.g., brominated fluoroethane compounds, such as, 2-bromo-2-chloro-1,1,1-trifluoroethane (CF₃CHBrCl).

In view of the well known lack of activity of chlorine which is found in a fluorinated chlorohydrocarbon, it is surprising that the chlorine-bromine exchange by which the bromo-fluoro and/or bromo-chloro-fluorohydrocarbons are formed can be effected in the gaseous phase by means of a catalyst, thereby avoiding the above-mentioned disadvantages which are attendant the process which is described in the U.S. Pat. No. 2,729,687.

As will be further demonstrated in the examples below, according to the process of the present invention, which can be carried out continuously, a compound of formula (I) can be reacted with hydrogen bromide according to the equation:

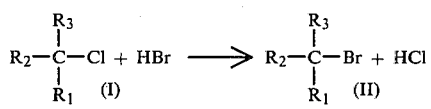

The process according to the present invention is preferably carried out at temperatures of between about 200° and 450° C., most preferably between about 300° and about 400° C.

Among the catalysts defined above, active carbon, and particularly active carbons having a metal bromide deposited thereon, are especially suited.

According to an embodiment of the present invention the reaction is effected in the presence of 0 to about 0.1 mole of hydrogen per mole of hydrogen bromide.

According to another embodiment of the invention the reaction is effected in the presence of 0 to about 0.1 mole of bromine per mole of hydrogen bromide.

The contact time between the reactants and the catalysts may be between about 1 and about 100, preferably between about 5 and about 50, and in particular, between about 10 and about 40 seconds.

If a compound of formula (Ia) is continuously reacted with hydrogen bromide according to the process of the present invention, the brominated reaction products may comprise a main product of formula (IIa) and a minor portion of a by-product of formula (IIb).

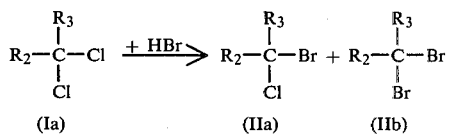

The latter and non-reacted starting material can be separated from the reaction product and continuously recycled into the process whereby a halogen interexchange with the starting material is effected according to the equation:

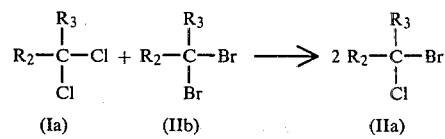

Thus, a remarkably high selectively can be achieved within a continuous brominating reaction according to the process of the present invention.

For example, dichloro-difluoromethane can be reacted continuously with hydrogen bromide according to the equation:

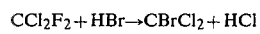

$CCl_2F_2 + HBr \rightarrow CBrClF_2 + HCl$ at a molar ratio between dichloro-difluoromethane and hydrogen bromide of 1.0 to 41 mole percent and at a temperature of only about 350° C. in contact with a catalyst consisting of active carbon and 45% by weight of zinc bromide for a contacting period of 11 seconds, whereby 36 mole percent of bromo-chloro-difluoromethane, 5 mole percent of dibromo-difluoromethane and 0.5 mole percent of dibromo-difluoromethane and 0.5 mole percent of other organic components (such as, trifluoromethane and chloro-trifluoromethane) relative to the amount of dichloro-difluoromethane which is used as a starting material are formed.

Together with the non-reacted starting materials, the dibromo-difluoromethane which is formed as a by-product according to the equation:

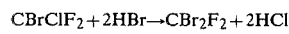

$CBrClF_2 + 2HBr \rightarrow CBr_2F_2 + 2HCl$ can be separated from the reaction mixture and can be continuously recycled over the catalyst, as is shown in Example 47. In this manner, the dibromo-difluoromethane is reacted with the dichloro-difluoromethane to form the desired bromo-chloro-difluoromethane according to the equation:

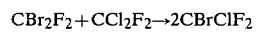

$CBr_2F_2 + CCl_2F_2 \rightarrow 2CBrClF_2$

Thus, finally an equilibrium concentration of dibromo-difluoromethane in the gaseous reaction product is reached. An extremely high selectively of the brominating reaction with a yield in bromo-chloro-difluoromethane of 98% are achieved. The catalyst has a long lifetime. After 674 operation hours, no marked loss in activity of the catalyst can yet be observed. Due to the relatively low reaction temperature of about 350° C., inexpensive materials can be used for building the reactor, for example, commonly available chromium-nickel steel is suitable.

The reaction product is separated into its components by conventional methods, preferably by distillation under pressure. According to a further separation method, the non-reacted hydrogen bromide and additional hydrogen chloride are reacted by adding chlorine to the gaseous reaction product and separating the different components according to the process which is described in the German Pat. No. 1,947,754, the disclosure of which is hereby incorporated by reference. The bromine which is recovered thereby can be used for preparing the starting hydrogen bromide.

The invention will now be further described with reference to the following examples, which are intended to be illustrative only.

EXAMPLES 1–45

Dichloro-difluoromethane and bromine are introduced into a tube reactor via a dosing rotameter and are reacted over various catalysts at temperatures of between 170° and 475° C., whereby different contact times are used. The reactors are made of nickel or quartz, respectively.

In Table I below, the catalysts and the reaction conditions are listed. The catalysts which are designated by numerals 1-9 are composed as follows:

(1) active carbon, Type Contarbon WS4, manufacturer Lurgi, (2) active carbon, grains, manufacturer Reidel de Haen, (3) active carbon, Type Norit RKD Special, manufacturer Norit, (4) active carbon, Type Contarbon W, manufacturer Lurgi, (5) $Al_2O_3$-activated, Type A 2/5, manufacturer Pechiney, (6) KC-($SiO_2$-gel)-Drying-Grains, manufacturer KALI-CHEMIE, (7) active carbon, grains, manufacturer Riedel de Haen, with the metal bromide deposited therein (defined in percent by weight), (8) active carbon, Type Contarbon WS4, manufacturer Lurgi, with $CaBr_2$ (defined in percent by weight) deposited thereon, and (9) active carbon, Type Norit RKD Special, manufacturer Norit, with 45% by weight of $ZnBr_2$ deposited thereon.

After being washed with water and sodium hydroxide solution, and dried over sulfuric acid, the reaction gases are analyzed and the organic components are determined by gas chromatography. The results are given in Table I below. Under most reaction conditions, the desired chloro-bromo-difluoromethane is the main product.

TABLE I

| | | Examples 1–45 | | | | | | |
|---|---|---|---|---|---|---|---|---|
| | | $CCl_2F_2$/ HBr — | React. | Contact | Organics in Reaction gas Mole % | | | |
| Test No. | Catalyst | molar ratio | Temp. (°C.) | time (sec.) | $CBrClF_2$ | $CBr_2F_2$ | $CCl_2F_2$ | Other compon. |
| 1 | A-carbon 1) | 0.65 | 400 | ~12 | 6 | 0.5 | 93 | 0.5 |
| 2 | A-carbon 1) | 0.65 | 450 | ~12 | 20 | 2 | 76 | 4 |
| 3 | A-carbon 2) | 0.65 | 400 | ~12 | 7 | — | 92 | 1 |
| 4 | A-carbon 2) | 0.65 | 475 | 10 | 21 | 1 | 70 | 8 |
| 5 | A-carbon 3) | 0.92 | 430 | 10 | 21 | 3 | 74 | 2 |
| 6 | A-carbon 4) | 0.65 | 450 | ~12 | 10 | 1 | 86 | 3 |
| 7 | $Al_2O_3$ 5) | 1.0 | 170 | 17 | 8 | 3 | 85 | 4 |
| 8 | $Al_2O_3$ 5) | 1.0 | 200 | 15 | 12 | 1 | 73 | 14 |
| 9 | $SiO_2$ 6) | 1.0 | 450 | ~10 | 5 | 3 | 88 | 4 |
| 10 | Pyrophillit | 1.0 | 350 | 11 | 2 | 0.5 | 97 | 0.5 |
| 11 | A-carbon + 40% LiBr 7) | 1.0 | 380 | 20 | 9 | 1 | | 0.5 |
| 12 | A-carbon + 20% NaBr 7) | 1.0 | 380 | 20 | 11 | 1 | 87 | 1 |
| 13 | A-carbon + 20% KBr 7) | 1.0 | 380 | 20 | 10 | 1 | 88 | 1 |
| 14 | A-carbon + 20% RbBr 7) | 1.0 | 380 | 20 | 13 | 1 | 85 | 1 |
| 15 | A-carbon + 40% CsBr 7) | 1.0 | 380 | 20 | 22 | 1 | 75 | 2 |
| 16 | A-carbon + 10% $MgBr_2$ 7) | 1.0 | 350 | 22 | 7 | 1 | 91 | 1 |
| 17 | A-carbon + 10% $CaBr_2$ 7) | 1.0 | 350 | 22 | 11 | 1 | 86 | 1 |
| 18 | A-carbon + 10% $CaBr_2$ 7) | 1.0 | 400 | 11 | 21 | 3 | 73 | 3 |
| 19 | A-carbon + 40% $CaBr_2$ 8) | 1.0 | 300 | 39 | 25 | 2 | 72 | 1 |
| 20 | A-carbon + 40% $CaBr_2$ 8) | 1.0 | 380 | ~11 | 21 | 4 | 73 | 2 |
| 21 | A-carbon + 10% $SrBr_2$ 7) | 1.0 | 360 | 22 | 8 | 1 | 91 | 0 |
| 22 | A-carbon + 10% $BaBr_2$ 7) | 1.0 | 360 | 22 | 7 | — | 92 | 1 |
| 23 | A-carbon + 40% (Mg—Ca—Sr—Ba—$Br_2$) 7) | 1.0 | 390 | 19 | 19 | 3 | 77 | 1 |
| 24 | A-carbon + 45% $ZnBr_2$ 7) | 1.0 | 300 | ~12 | 12 | 3 | 85 | 0.1 |
| 25 | A-carbon + 45% $ZnBr_2$ 7) | 1.0 | 320 | ~12 | 21 | 7 | 72 | 0.2 |
| 26 | A-carbon + 45% $ZnBr_2$ 7) | 1.0 | 350 | ~11 | 33 | 5 | 62 | 0.4 |
| 27 | A-carbon + 45% $ZnBr_2$ 9) | 1.0 | 350 | ~11 | 36 | 5 | 59 | 1.5 |
| 28 | A-carbon + 50% $ZnBr_2$ 7) | 1.5 | 350 | 20 | 39 | 10 | 49 | 2 |
| 29 | A-carbon + 50% $ZnBr_2$ 7) | 1.5 | 320 | 17 | 31 | 7 | 62 | — |
| 30 | A-carbon + 50% $ZnBr_2$ 7) | 2.0 | 320 | 21 | 21 | 2 | 77 | — |
| 31 | A-carbon + $ZnBr_2$ 7) | 4.0 | 320 | 21 | 19 | 1 | 80 | — |
| 32 | A-carbon + 45% $CdBr_2$ 7) | 1.0 | 320 | 21 | 26 | 2 | 72 | — |
| 33 | A-carbon + 45% $CuBr_2$ 7) | 1.0 | 400 | 10 | 27 | 4 | 63 | 2 |
| 34 | A-carbon + 30% $AgNO_3$ 7) | 1.0 | 350 | 11 | 18 | 5 | 74 | 3 |
| 35 | A-carbon + 15% $AlCl_3$ 7) | 1.0 | 280 | 13 | 5 | 2 | 91 | 2 |
| 36 | A-carbon + 45% $ZnCl_2$ 7) | 1.0 | 350 | 11 | 29 | 4 | 66 | 1 |
| 37 | A-carbon + 25% TlBr 7) | 1.0 | 350 | 20 | 11 | 4 | 83 | 2 |
| 38 | A-carbon + 40% $PbBr_2$ 7) | 1.0 | 300 | 24 | 21 | 3 | 75 | 1 |
| 39 | A-carbon + 10% $CrBr_3$ 7) | 1.0 | 400 | 19 | 23 | 4 | 65 | 8 |
| 40 | A-carbon + 10% $SEBr_3$ 7) | 1.0 | 300 | 24 | 5 | 1 | 93 | 1 |
| 41 | A-carbon + 40% $FeCl_3$ 7) | 1.0 | 275 | 13 | 30 | 3 | 62 | 5 |
| 42 | A-carbon + 30% $CoCl_2$ 7) | 1.0 | 400 | 10 | 18 | 3 | 64 | 3 |
| 43 | A-carbon + 30% $NiCl_2$ 7) | 1.0 | 425 | 10 | 20 | 3 | 64 | 3 |
| 44 | A-carbon + 45% $Zn(BF_4)_2$ 7) | 1.0 | 350 | 11 | 35 | 7 | 57 | 1 |
| 45 | A-carbon + 50% (Cu—, Ca—, Zn—$Br_2$) 7) | 1.0 | 350 | 11 | 31 | 4 | 65 | 1 |

EXAMPLE 46

In a quartz reactor, dichloro-difluoromethane, dibromo-difluoromethane and hydrogen bromide (molar ratio 1:1:1) are reacted over a catalyst consisting of active carbon (type Norit RKD Special, manufacturer Norit) onto which 40% by weight of zinc bromide are deposited for a contact time of 16 seconds, at a reaction temperature of 320° C. After removal of acids by washing and drying, the reaction gas contains 31 mole percent of dichloro-difluoromethane, 28 mole percent of bromo-chloro-difluoromethane and 41 mole percent of dibromo-difluoromethane.

EXAMPLE 47

In a nickel reactor containing a catalyst consisting of active carbon (type Norit RKD Special, manufacturer Norit) onto which 45% by weight of zinc bromide are deposited, chloro-trifluoromethane and hydrogen bromide (molar ratio 1:1) are reacted at a reaction temperature of 400° C. and a contact time of 15 seconds. After removal of the hydrogen halogenides, 27 mole percent of bromo-trifluoromethane and 73 mole percent of non-reacted chloro-trifluoromethane are found in the reaction product by gas chromatography.

EXAMPLE 48

In a quartz reactor which is filled with a catalyst containing 50% by weight of active carbon (type Norit RKD Special, manufacturer Norit), 25% by weight of zinc bromide and 25% by weight of calcium bromide, chloro-trifluoromethane and hydrogen bromide (molar ratio 1:1.2) are reacted at a temperature of 400° C. and a contact time of 22 seconds. 36 mole percent of bromo-trifluoromethane and 64 mole percent of non-reacted chloro-trifluoromethane are found in the organic reaction product.

EXAMPLE 49

In a nickel reactor containing a catalyst consisting of active carbon onto which 45% by weight of zinc bromide are deposited, chloro-penta-fluoroethane and hydrogen bromide (molar ratio 1:1) are reacted at a temperature of 450° C. and a contact time of 15 seconds. The reaction gas is washed with water and sodium hydroxide solution and subsequently dried over sulfuric acid. In the dried acid-free reaction gas, 13 mole percent of bromo-penta-fluoroethane and 87 mole percent of chloro-penta-fluoroethane are found. No by-products are formed.

EXAMPLE 50

In the above-described reactor, 2,2-dichloro-1,1,1-trifluoroethane and hydrogen bromide (molar ratio 1:1) are reacted over a catalyst containing 55% by weight of active carbon and 45% by weight of zinc bromide at a temperature of 350° C. and a contact time of 15 seconds. As determined by gas chromatography, the dried reaction gas contains 26 mole percent of 2-bromo-2-chloro-1,1,1-trifluoroethane and 9 mole percent of 2,2-dibromo-1,1,1-trifluoroethane in addition to non-reacted starting materials.

While the invention has now been described in terms of various preferred embodiments, and exemplified with respect thereto, the skilled artisan will readily appreciate that various substitutions, changes, modifications, and omissions, may be made without departing from the spirit thereof. Accordingly, it is intended that the scope of the invention be limited solely by that of the following claims.

What is claimed is:

1. A process for brominating fluorine- and chlorine-containing halogenated hydrocarbons, which comprises the step of contacting a vapor phase mixture, comprising a halogenated fluorohydrocarbon compound selected from dichloro-difluoromethane, chloro-trifluoromethane or 2,2-dichloro-1,1,1-trifluoroethane, and hydrogen bromide, with a catalyst comprising a mixture of active carbon and at least one bromide of a metal selected from the group consisting of Zn, and Cd at a contact time and a reaction temperature of from about 100° C. to about 500° C. which is sufficient for substituting the chlorine in said halogenated fluorohydrocarbon compound by bromine to form
   (a) bromo-chloro-difluoromethane in the case of dichloro-difluoromethane,
   (b) bromo-trifluoromethane in the case of chloro-trifluoromethane, or
   (c) 2-bromo-2-chloro-1,1,1-trifluoroethane in the case of 2,2-dichloro-1,1,1-trifluoroethane.

2. The process as defined by claim 1, wherein bromo-chloro-difluoromethane is obtained from dichloro-difluoromethane.

3. The process as defined in claim 1, wherein bromo-trifluoromethane is obtained from chloro-trifluoromethane.

4. The process as defined in claim 1, wherein 2-bromo-2-chloro-1,1,-trifluoroethane is obtained from 2,2-dichloro-1,1,1-trifluoroethane.

5. A process for brominating fluorine- and chlorine-containing halogenated hydrocarbons, which comprises the steps of:
   contacting a vapor phase mixture, comprising a halogenated fluorohydrocarbon compound selected from dichloro-difluoromethane or 2,2-dichloro-1,1,1-trifluoroethane, and hydrogen bromide, with a catalyst comprising a mixture of active carbon and at least one bromide of a metal selected from the group consisting of Zn, and Cd at a contact time and a reaction temperature of from about 100° C. to about 500° C. which is sufficient for substituting the chlorine in said fluorohydrocarbon compound by bromine, and continuously recycling a mixture of non-reacted starting material and a dibrominated reaction product into said contacting step, wherein said dibrominated reaction product is selected from
   (a) dibromo-difluoromethane obtained during the bromination of dichloro-difluoromethane, whereby bromo-chloro-difluoromethane is formed, and
   (b) 2,2-dibromo, 1,1,1-trifluoroethane obtained during the bromination of 2,2-dichloro-1,1,1-trifluoroethane, whereby 2-bromo-2-chloro-1,1,1-trifluoroethane is formed.

6. The process as defined in claim 5, wherein dibromo-difluoromethane which is obtained during the bromination of dichloro-difluoromethane is recycled into the reaction step, whereby bromo-chloro-difluoromethane is formed.

7. The process as defined in claim 5, wherein 2,2-dibromo-1,1,1-trifluoroethane which is obtained during the bromination of 2,2-dichloro-1,1,1-trifluoroethane is recycled into the reaction step, whereby 2-bromo-2-chloro-1,1,1-trifluoroethane is formed.

* * * * *